(12) United States Patent
Hahn et al.

(10) Patent No.: US 7,617,544 B2
(45) Date of Patent: Nov. 17, 2009

(54) PROTECTIVE EYEWEAR

(75) Inventors: Helen M. Hahn, Catonsville, MD (US); Dale W. Kohler, Hunt Valley, MD (US)

(73) Assignee: WM. T. Burnett IP, LLC, Baltimore, MD (US)

( * ) Notice: Subject to any disclaimer, the term of this patent is extended or adjusted under 35 U.S.C. 154(b) by 190 days.

(21) Appl. No.: 11/832,366

(22) Filed: Aug. 1, 2007

(65) Prior Publication Data

US 2008/0016600 A1 Jan. 24, 2008

Related U.S. Application Data

(62) Division of application No. 11/001,139, filed on Dec. 2, 2004, now Pat. No. 7,260,854.

(51) Int. Cl.
*A61F 9/02* (2006.01)
(52) U.S. Cl. .............................. 2/431; 2/425
(58) Field of Classification Search .................. 2/9, 2/427–429, 425, 431, 6.3
See application file for complete search history.

(56) References Cited

U.S. PATENT DOCUMENTS

| 924,613 | A | | 6/1909 | Hellawell | |
|---|---|---|---|---|---|
| 1,186,442 | A | | 6/1916 | Schaefer | |
| 2,206,997 | A | * | 7/1940 | Austad | .............................. 2/9 |
| 4,173,795 | A | | 11/1979 | Lundin et al. | |
| 4,279,038 | A | | 7/1981 | Bruckner et al. | |
| 4,333,179 | A | | 6/1982 | Laurita | |
| 5,249,347 | A | | 10/1993 | Martinitz | |
| 5,267,353 | A | | 12/1993 | Milliganm | |
| 5,661,849 | A | * | 9/1997 | Hicks | .............................. 2/9 |
| 5,966,744 | A | * | 10/1999 | Smith, Jr. | ........................ 2/424 |
| 6,301,719 | B1 | * | 10/2001 | Goodhand et al. | ............. 2/422 |
| 6,598,234 | B1 | | 7/2003 | Brown et al. | |
| 6,715,157 | B2 | | 4/2004 | Mage | |
| 7,127,474 | B2 | | 10/2006 | Darnell et al. | |
| 7,222,370 | B2 | * | 5/2007 | Gait | .............................. 2/9 |
| 7,260,854 | B2 | * | 8/2007 | Hahn et al. | ..................... 2/431 |
| 7,322,692 | B2 | * | 1/2008 | Winningham | ............... 351/156 |
| 2004/0133958 | A1 | | 7/2004 | Darnell et al. | |
| 2007/0266471 | A1 | * | 11/2007 | Lin | .................................. 2/9 |
| 2009/0044318 | A1 | * | 2/2009 | Spagna et al. | .................. 2/425 |

OTHER PUBLICATIONS

Article entitled "Comparing the Top End—A Tale of Two Masks" by Brent mcLaren dated Mar. 5, 2000; http://www.amateurumpire.com/equip/masks.htm.

* cited by examiner

*Primary Examiner*—Katherine Moran
(74) *Attorney, Agent, or Firm*—Paul, Hastings, Janofsky & Walker LLP

(57) ABSTRACT

A protective eyewear apparatus including a base substantially oval in shape, an upper bar connected to the base, a lower bar connected to the base, and a main support bar connected to the upper bar and the lower bar. Another embodiment includes two eyepieces attached by a flexible bridge member, in which an eyepiece comprises a base generally oval in shape and defining an opening, and an upper and lower bar spanning the opening and connected to the base.

32 Claims, 13 Drawing Sheets

PROTECTIVE EYEWEAR

This application is a division of U.S. patent application Ser. No. 11/001,139, filed Dec. 2, 2004, now U.S. Pat. No. 7,260,854 which is herein incorporated by reference in its entirety.

BACKGROUND

1. Field of the Invention

The present invention relates generally to protective eyewear, and more particularly, to a protective eyewear apparatus for sports such as women's lacrosse or field hockey.

2. Background of the Invention

Protecting players from injury is a primary concern for any sport. The most vulnerable part of the body is the head, face, and eyes. Thus, protective face masks and eyewear are common in sports such as baseball, hockey, football, racquetball, squash, and lacrosse.

In lacrosse, the hard, heavy rubber lacrosse ball can cause significant injury to unprotected eyes and faces. Most generally accepted rules for competitive lacrosse require a lacrosse ball made of solid rubber, between 7¾ and 8 inches in circumference (about 2½ inches in diameter), and between 5 and 5¼ ounces in weight. Because the lacrosse balls are routinely thrown at high speeds and with great force, the impact of the balls can cause bruises, broken bones, and, in rare cases, even death. Indeed, in addition to the long-standing requirement for helmets with face masks in men's lacrosse, protective eyewear is now mandatory in women's lacrosse.

In general, manufacturers are continually striving to improve the impact resistance of protective eyewear. Improvements in the strength of the equipment, however, often cause the equipment to be too stiff, bulky, or obtrusive, and uncomfortable to wear. This discomfort can cause a player to wear the equipment improperly or not at all, thereby defeating any improvement in protection.

Overall, protective eyewear should be comfortable to wear on a continuous basis and should provide protection meeting the applicable standards for its usage, such as ASTM F 803-03 impact requirements. In providing comfort, the eyewear should be lightweight, flexible, and comfortable against the skin, and should provide adequate ventilation allowing the user to dissipate heat and moisture.

BRIEF SUMMARY OF THE INVENTION

An embodiment of the present invention provides a protective eyewear apparatus including a base, a protective cage, and a main support bar. The base can be substantially oval in shape, such that the base can surround the eyes of a user wearing the protective eyewear apparatus. The protective cage can include an upper bar connected to the base and a lower bar connected to the base. The main support bar can be connected to the upper bar and the lower bar. Optionally, the upper bar has no more than the three connections to the base and the main support bar, and the lower bar has no more than the three connections to the base and the main support bar.

In a further embodiment, the base can include a generally straight forehead member, and a generally arcuate cheek member having a first end connected to the forehead member and a second end connected to the forehead member to form the substantially oval shape.

In another embodiment, the base can include a forehead member and a cheek member. The cheek member can have a generally arcuate shape and have a first and second end connected to the forehead member. The protective cage can include an upper bar and a lower bar. The upper bar has a first and second end connected to the cheek base member. The lower bar has a first and second end connected to the cheek base member. The upper bar is disposed closer to the forehead base member than the lower bar. The main support bar can be connected to the forehead base member, the upper bar, the lower bar, and the cheek base member.

A further embodiment of the present invention includes a compressible layer disposed on at least a portion of the base, for example, in areas at which the base is intended to contact a user's skin. In one implementation, a first compressible layer is disposed on the forehead member and a second compressible layer is disposed on the cheek member. The upper and lower bars of the protective cage and the main support bar can also be covered with a compressible layer.

A compressible layer can be, for example, a foam (e.g., open or closed cell) or elastomer. An elastomer can be overmolded onto the members of the eyewear apparatus. On the base members, the compressible layer is in contact with the user's face, and provides a compressible outer surface that conforms comfortably to the contours of a user's face. In a further embodiment, the compressible layer on the base members defines gutters that channel perspiration away from the user's eyes, nose, and mouth. In another embodiment, the compressible layer has a textured surface, with raised portions of the textured surface contacting a user's skin and depressed portions of the textured surface holding perspiration.

In a further embodiment of the present invention, the protective eyewear apparatus includes a layer of performance fabric over the compressible layer. This performance fabric can be disposed over the portions of the eyewear apparatus that contact the user, such as locations at which the eyewear contacts the user's cheeks.

In an embodiment of the invention, the frame has only one vertical protective bar in the user's field of vision, located substantially over the nose of the user. By minimizing vertical members and strategically sizing, spacing, and locating the protective bars, the frame of the present invention defines a wide unobstructed viewing area that extends around the sides of the user's eyes. This unobstructed area maximizes the user's field of vision, in directions straight ahead, up and down, and peripherally. At the same time, the protective bars of the frame prevent a standard sized lacrosse ball from impacting a user's eye and enable the present invention to comply with generally accepted rules on the construction of protective eyewear, such as the requirements of ASTM F803-03, the Protective Eyewear Certification Council (PECC), U.S. Lacrosse, and the National Federation of High Schools (NFHS).

In a further embodiment of the present invention, the protective eyewear apparatus also includes four more support bars interconnecting the base and the protective cage, in addition to the main support bar.

An alternative embodiment of the present invention provides a protective eyewear apparatus having two eyepieces attached by a flexible bridge member. An eyepiece comprises a base generally oval in shape and defining an opening, and an upper and lower bar spanning the opening.

BRIEF DESCRIPTION OF THE DRAWINGS

FIG. 8 is a schematic diagram of a cross-sectional view of the frame shown in FIG. 2 along line C-C.

DETAILED DESCRIPTION OF THE INVENTION

Figure 1A:
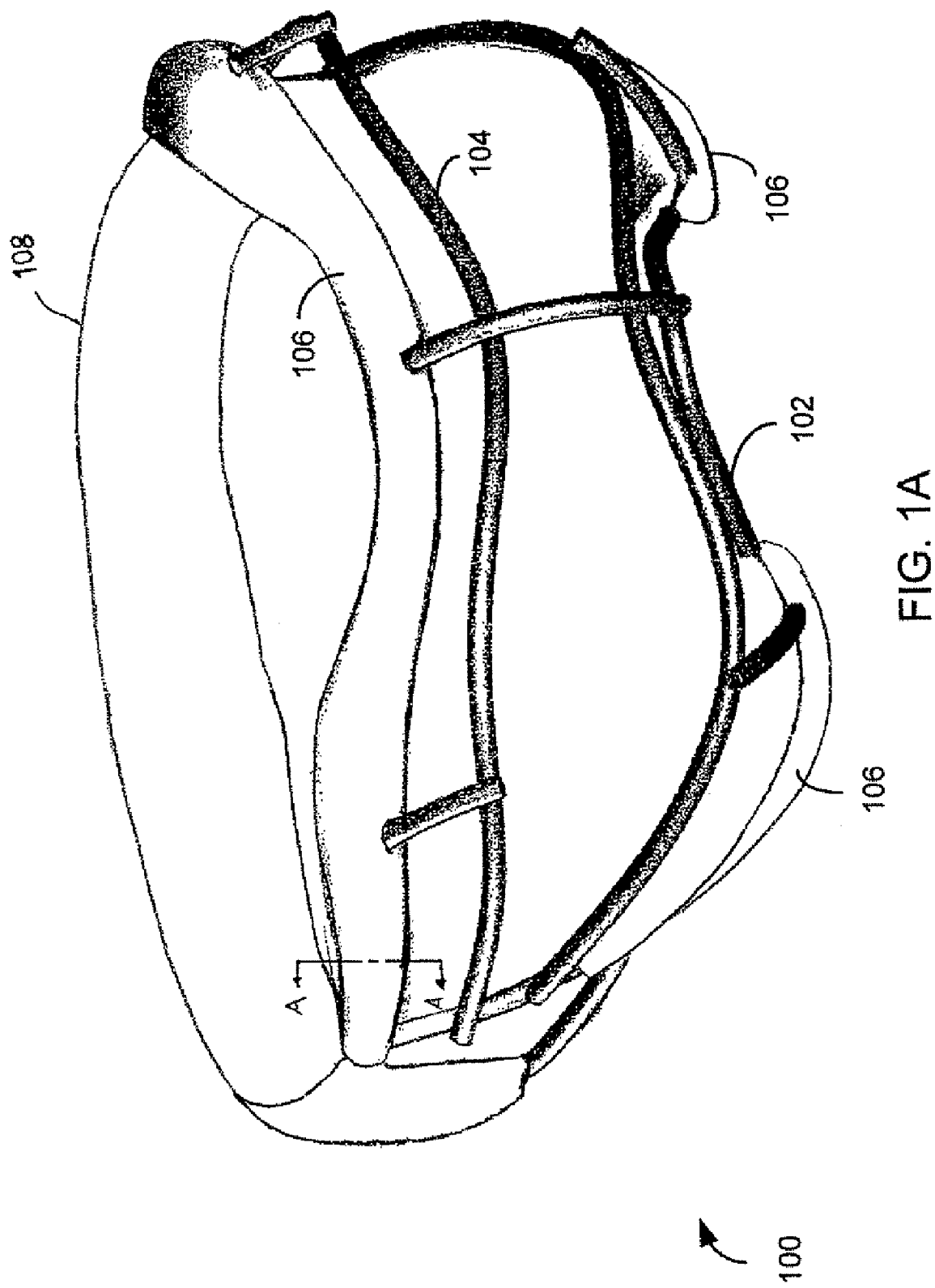
FIG. 1A is a schematic diagram of an isometric view of an exemplary protective eyewear apparatus, according to an embodiment of the present invention.
Figure 1B:
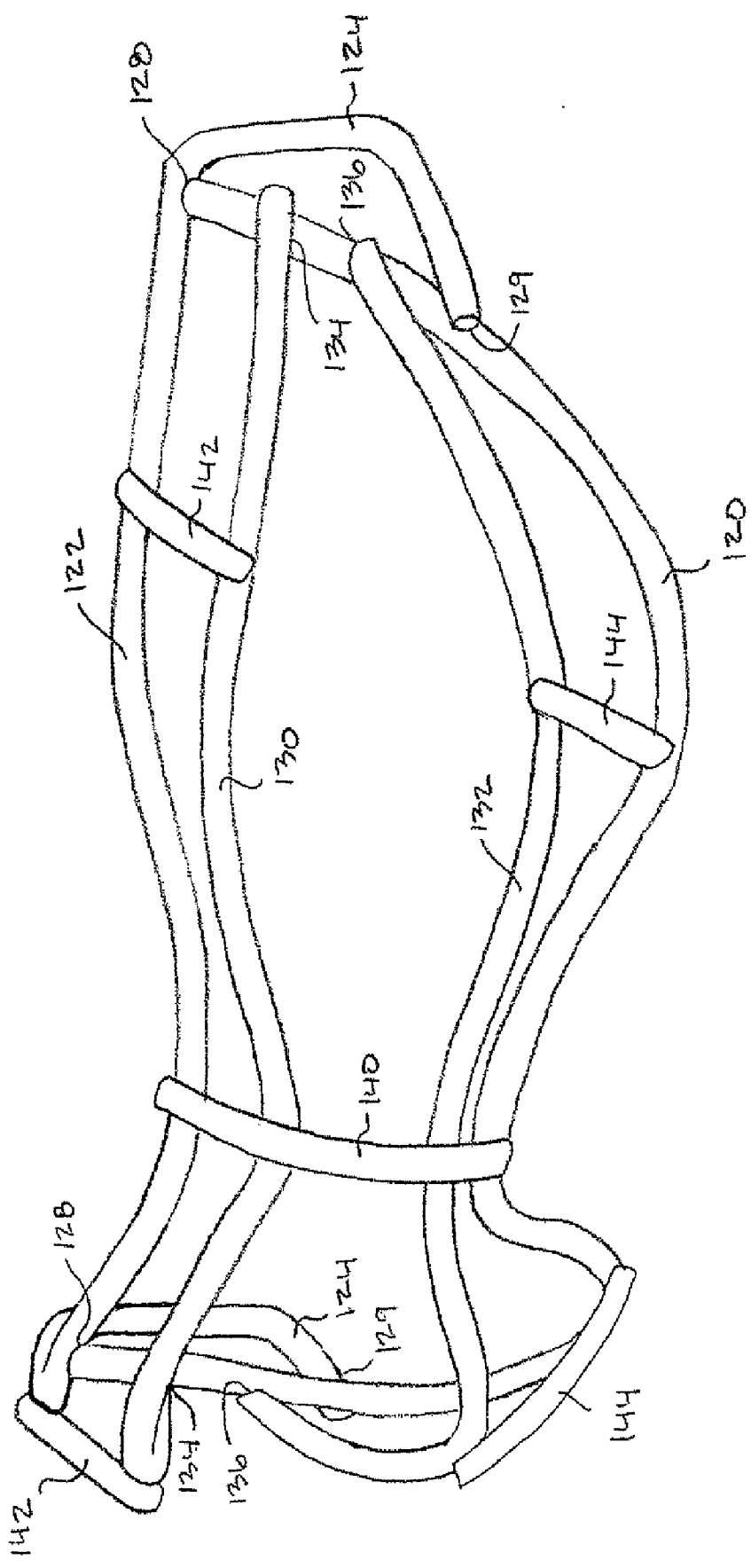
FIG. 1B is a schematic diagram of an isometric view of the frame of the protective eyewear apparatus shown in FIG. 1A, according to an embodiment of the present invention.

FIG. 1A is a schematic diagram of an isometric view of an exemplary protective eyewear apparatus 100, according to an embodiment of the present invention. As shown, eyewear apparatus 100 includes a base 102, a protective cage 104, compressible layers 106, and securing means 108. Base 102 and protective cage 104 provide the frame of eyewear apparatus 100 and can be made of weldable and bendable steel, such as 3.8 mm 1008 solid carbon steel wire, ASTM Standard, Section 03.05. Other suitable materials include other metals, metal alloys, composite materials, and synthetic materials. In this example, compressible layers 106 are disposed on base 102 in areas at which eyewear apparatus 100 contacts the face of a user, along the inferior forehead and the zygomatic arch (the temporal bone of the skull that forms the prominence of the cheek). Compressible layers 106 could be separate pieces located at each area of contact (e.g., forehead and zygomatic arch) of base 106 or could be one continuous piece covering base 106. Protective cage 104 is elevated away from the face of the user and can optionally also be covered by a compressible layer.

FIGS. 1B-8 are schematic diagrams that illustrate the base 102 and protective cage 104 in more detail, with the compressible layers 106 not shown. As shown in these figures, base 102 includes a cheek base member 120 and a forehead base member 122. Forehead base member 122 can include a center portion 200 and two strap portions 124 for attaching a securing means 108 (FIG. 1A) to the eyewear apparatus 100. This securing means could be any well known means for securing goggles, eyeglasses, or other eyewear apparatus to a user's face, for example, an elastic strap.

In an embodiment of the present invention, forehead base member 122 and strap members 124 are formed from a single continuous member and cheek base member 120 is formed from another single continuous member, with the two continuous members attached at points 128. In this embodiment, forehead base member 122 has a center portion 200 with a first strap portion 124 on one side of the center portion 200 and a second strap portion 124 on the opposite side. Cheek base member 120 is generally arcuate in shape, as shown best in FIG. 2, and connects to forehead base member 122 approximately between the center portion 200 and the first strap portion 124 and between the center portion 200 and the second strap portion 124. The strap portions 124 provide means for securing a strap or other suitable securing means to the base 102 of the protective eyewear apparatus 100. Optionally, the strap portions 124 are further attached to the cheek base member 120 at points 129 to form closed loops, e.g., on which a strap can be mounted.

Figure 5:
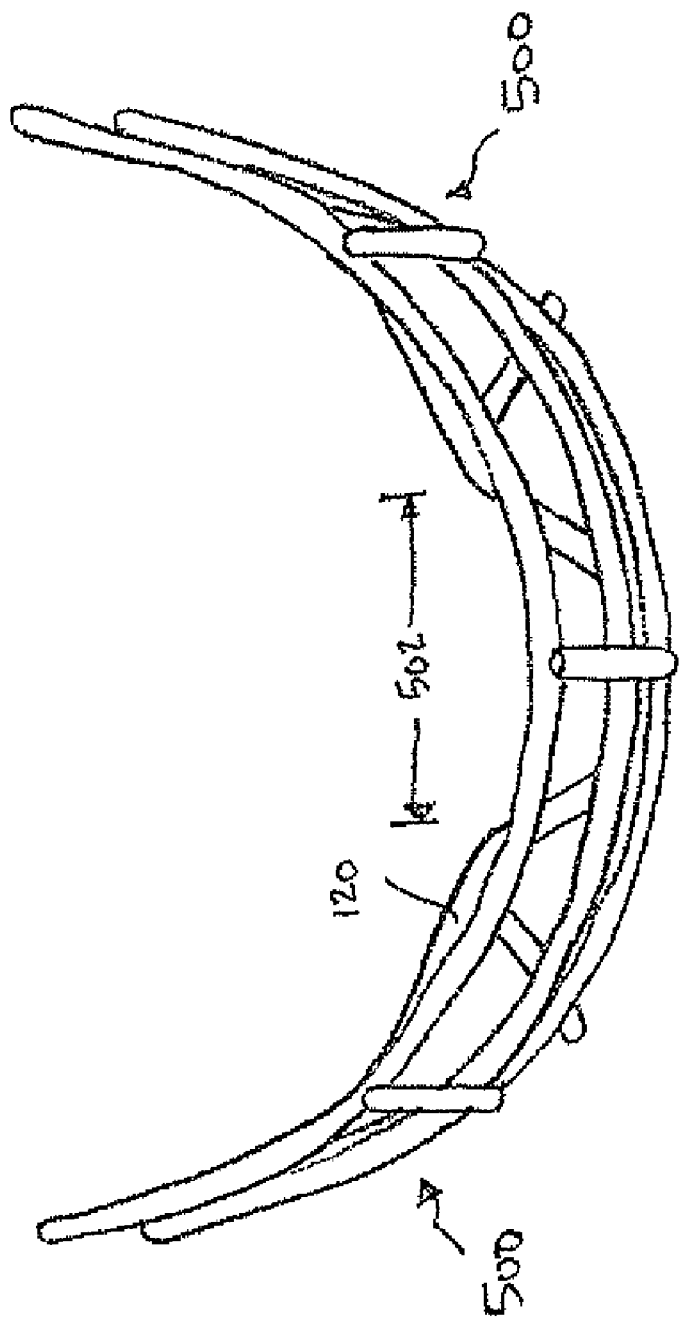
FIG. 5 is a schematic diagram of a top view of the frame shown in FIG. 1B.

In a further aspect of the present invention, cheek base member 120 includes a projecting portion 502 as shown best in FIG. 5. This projecting portion 502 spans a user's nose such that the protective eyewear apparatus does not contact the user's nose when the protective eyewear apparatus is worn by the user. For this reason, the projecting portion 502 does not need a compressible layer and can remain uncovered as is shown in FIG. 1A. This aspect makes the protective eyewear apparatus of the present invention more comfortable to wear.

Protective cage 104 includes an upper bar 130 and a lower bar 132, both of which are substantially horizontal and are attached at their ends to cheek base member 120 at points 134 and 136, respectively. Upper bar 130 is disposed closer to forehead base member 122 than lower bar 132. As shown by the side views of FIGS. 3 and 4, bars 130 and 132 are positioned outward of base 102 relative to the user's face. In this manner, bars 130 and 132 prevent a lacrosse ball from contacting a user's eye. Positioning bars 130 and 132 farther out from base 102 (as opposed to closer in) enables bars 130 and 132 to be spaced farther apart, therefore presenting less of an obstruction to the user's view. In an embodiment of the present invention, the opening defined by the protective cage 104 prevents objects larger than 2¼ inches from passing into the protective cage 104.

To further strengthen upper bar 130 and lower bar 132, eyewear apparatus 100 can include a main support bar 140 that is attached to both upper bar 130 and also lower bar 132. The main support bar 140 can also be attached to forehead base member 122 and cheek base member 120. Main support bar 140 can be substantially vertical and attach approximately to the centers of forehead base member 122, upper bar 130, lower bar 132, and cheek base member 120.

To provide additional support between base 102 and protective cage 104, eyewear apparatus 100 can also include upper support bars 142 that are connected to forehead base member 122 and upper bar 130, and lower support bars 144 that are connected to cheek base member 120 and lower bar 132.

Main support bar 140 can be located substantially over the user's nose. Each of upper support bars 142 can be located approximately the same distance from main support bar 140. Likewise, each of lower support bars 144 can be located approximately the same distance from main support bar 140.

An alternative embodiment of the present invention provides a protective eyewear apparatus having no support bars (such as main support bar 140, upper support bars 142, or lower support bars 144). Instead, this alternative embodiment has only upper bar 130, lower bar 132, cheek base member 120, and forehead base member 122. To provide adequate protection against the impact of a lacrosse ball, these members can be constructed of a material sufficiently strong enough not to deflect or deform upon impact by the ball. In one embodiment, these members can be made of 1008 solid carbon steel wire of a sufficient thickness or of a composite resin, such as the composite resin bars used on the SUL200™ mask produced by +POS of Schaumburg, Ill.

Another alternative embodiment of the present invention provides a protective eyewear apparatus having only one vertical support bar (such as the main support bar 140) connected to the forehead base member 122, upper bar 130, lower bar 132, and cheek base member 120, without additional support bars such as upper support bars 142 and lower support bars 144. In this case, upper bar 130 and lower bar 132 would have only three connections: two connections at their ends to cheek base member 120 and one connection at an intermediate location to the one vertical support bar (such as the main support bar 140). To provide adequate protection against the impact of a lacrosse ball, these members can be constructed of a material sufficiently strong enough not to deflect or deform upon impact by the ball. In one embodiment, these members can be made of 1008 solid carbon steel wire of a sufficient thickness or of a composite resin, such as the composite resin bars used on the SUL200™ mask produced by +POS of Schaumburg, Ill.

With reference to FIGS. 1A-8, in an implementation of the present invention that meets or exceeds the ASTM standard for women's adult and youth lacrosse (ASTM F803-03, which is herein incorporated by reference in its entirety), the base 102 and protective cage 104, including main support bar 140, upper support bars 142, and lower support bars 144, are made of 3.8 mm diameter 1008 solid carbon steel wire (ASTM Standard, Section 03.05). The wire is cut to the desired length for each member. The cut wires are then bent and pressed into the desired shapes, such as those shown in FIGS. 1B through 8. The shaped wires are then placed on a welding jig and welded point by point. The welded members are then trimmed, polished, and coated with a polyester powder about 50 to 100 microns thick. Also according to this implementation, the compressible layers 106 are made of a silicone foam compound and the eyewear apparatus 100 has the dimensions set forth below.

Figure 3:
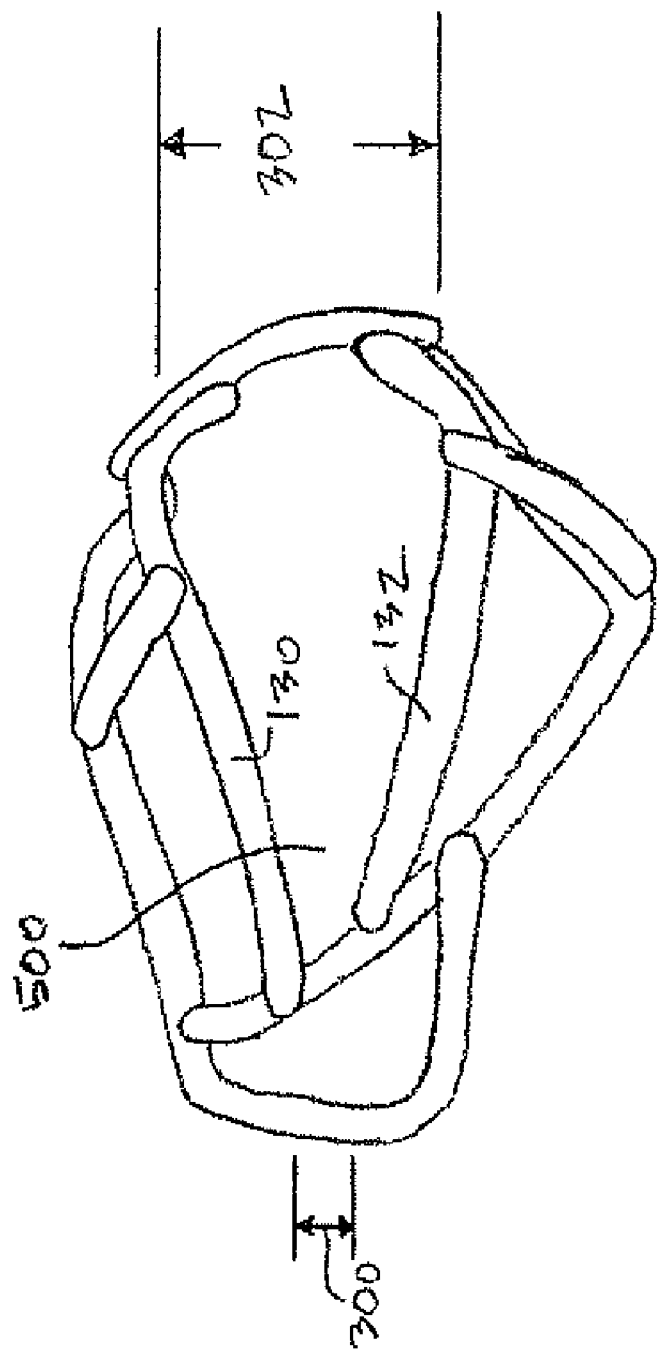
FIG. 3 is a schematic diagram of a right side view of the frame shown in FIG. 1B.

Referring to FIG. 3, the narrowest distance 300 between the upper and lower bars 130 and 132 is about 0.261 inches and the widest distance 302 between the upper and lower bars 130 and 132 is about 1.324 inches.

Figure 2:
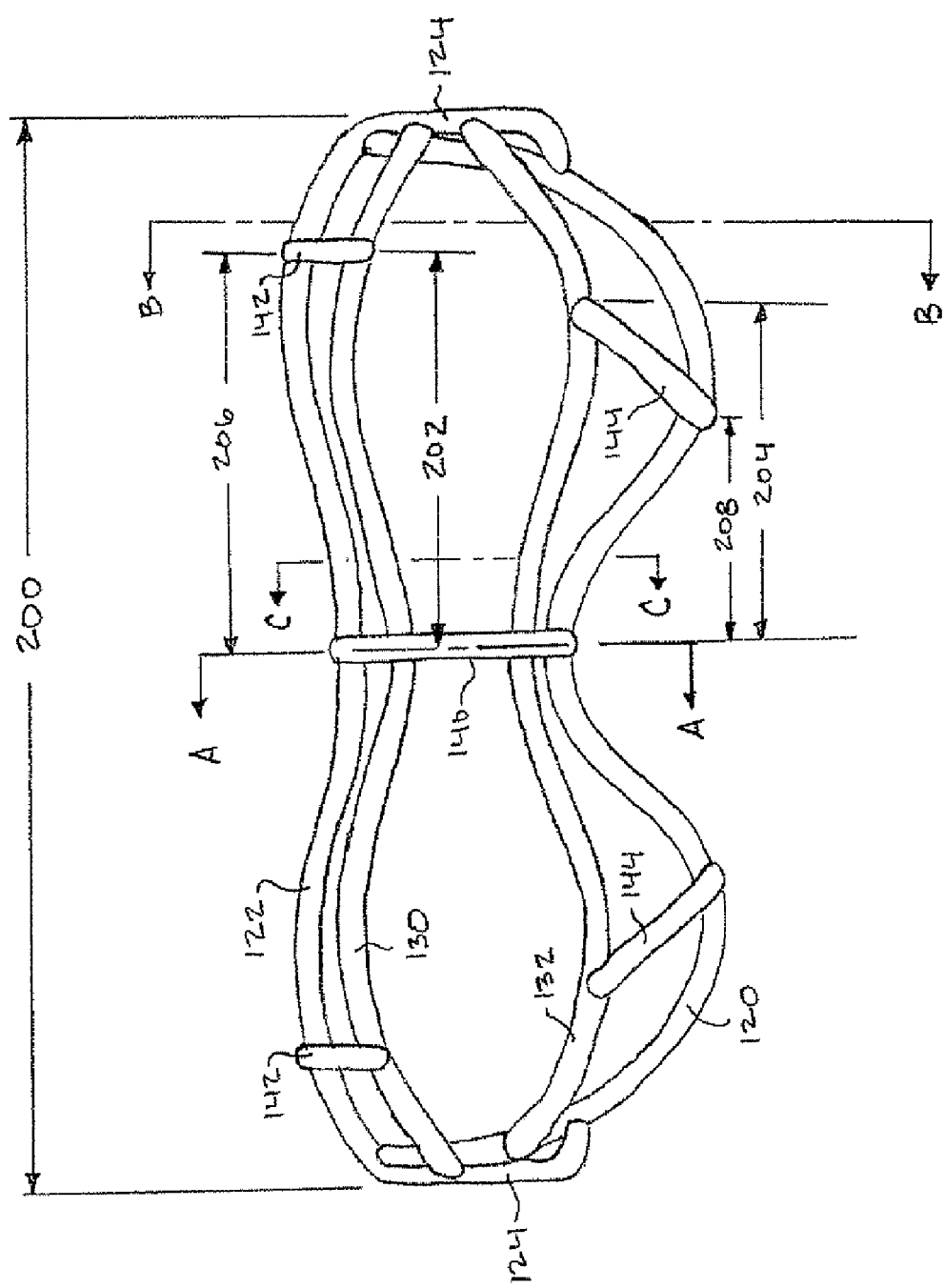
FIG. 2 is a schematic diagram of a front view of the frame shown in FIG. 1B.

Referring to FIG. 2, the total horizontal distance of the center portion 200 from the left strap member 124 to the right strap member 124 is about 5.970 inches. The distance 202 from the main support bar 140 to the lower most part of the upper support bar 142 is about 2.254 inches. The distance 204 from the main support bar 140 to the upper most point of the lower support bar 144 is about 1.903 inches. The distance 206 from the main support bar 140 to the upper most point of the upper support bar 142 is about 2.252 inches. The distance 208 from the main support bar 140 to the lower most point of the lower support bar 144 is about 1.276 inches.

Figure 4:
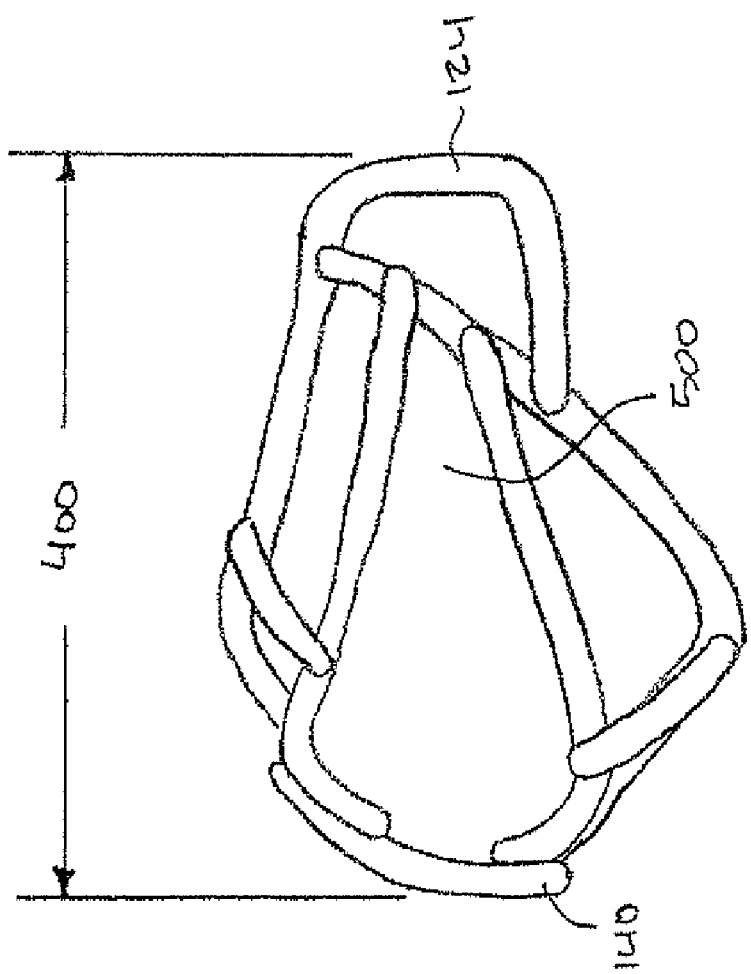
FIG. 4 is a schematic diagram of a left side view of the frame shown in FIG. 1B.

Referring to FIG. 4, the total depth 400 from the outer most point of the main support bar 140 to the most rearward point of the strap member 124 is about 3.427 inches.

Figure 6:
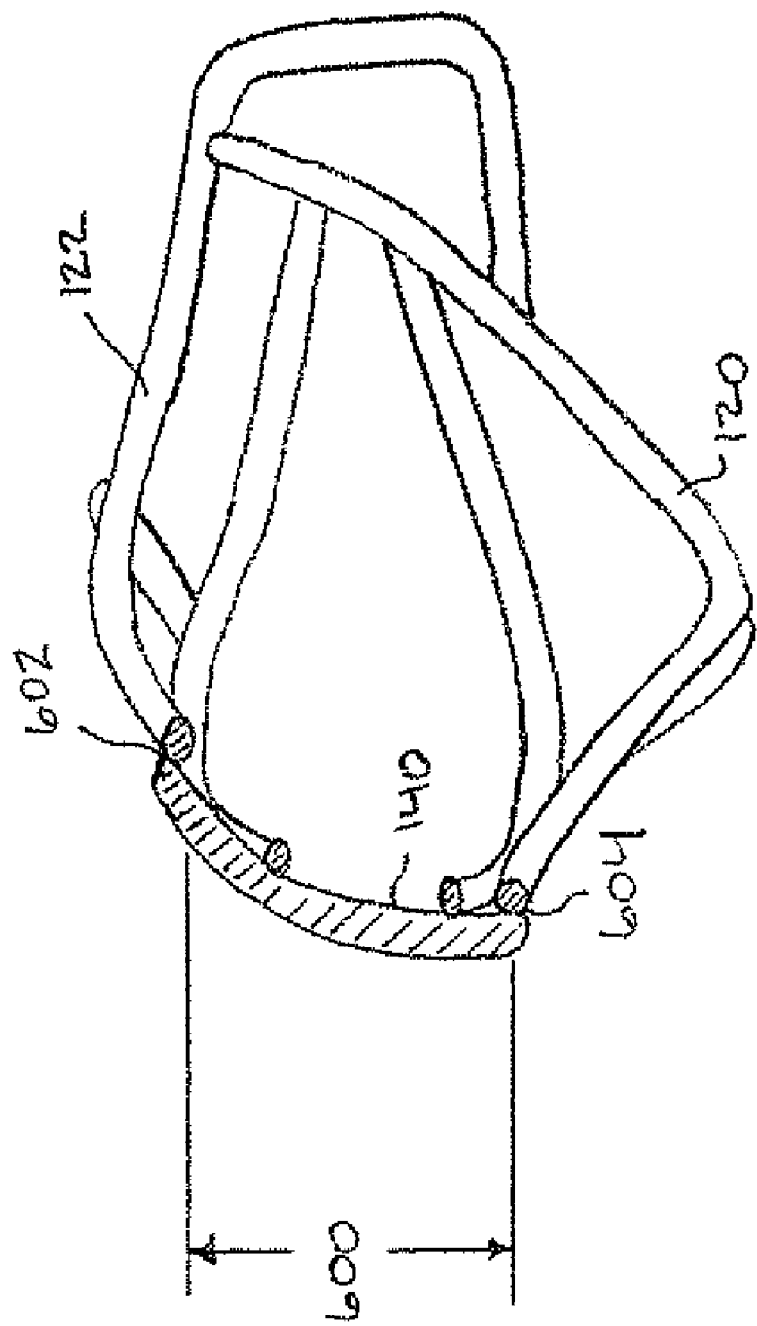
FIG. 6 is a schematic diagram of a cross-sectional view of the frame shown in FIG. 2 along line A-A.

Referring to FIG. 6, the distance 600 from the intersection 602 of the forehead base member 122 and the main support bar 140 to the intersection 604 of the cheek base member 120 and the main support bar 140 is about 1.156 inches.

Finally, the overall outer dimension of the compressible layers 106 shown in FIG. 1A can be approximately 0.55 inches, with a thickness of about 0.28 inches covering forehead base member 122 or cheek base member 120. The outer dimension and thickness covering the members can, of course, vary as required to provide the desired cushioning. The position of the members within the compressible layers 106 can also vary, for example, being concentric in some locations and non-concentric in others.

With these materials of construction and dimensions, the present invention provides comfortable eyewear that protects a user from the impact of a standard lacrosse ball, in compliance with the ASTM F803-03 standard. The configuration of the protective cage 104 also enables a wide field of vision obstructed only by one vertical member (main support member 140) and open on both sides of the head for unhindered peripheral vision. FIGS. 3-5 best illustrate this unobstructed field of peripheral vision 500.

Figure 7:
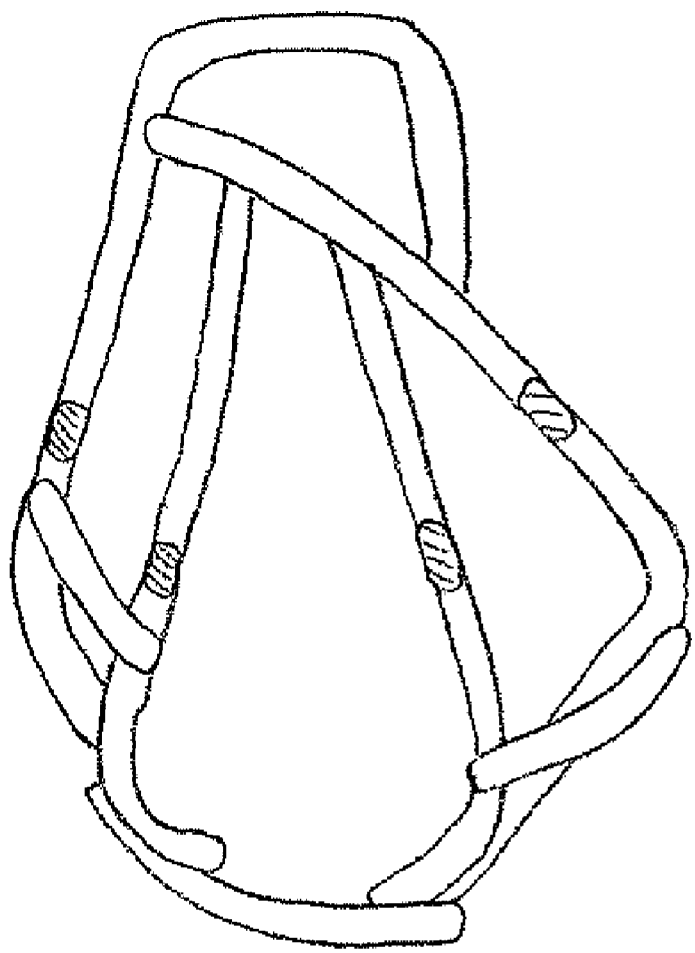
FIG. 7 is a schematic diagram of a cross-sectional view of the frame shown in FIG. 2 along line B-B.
Figure 6:
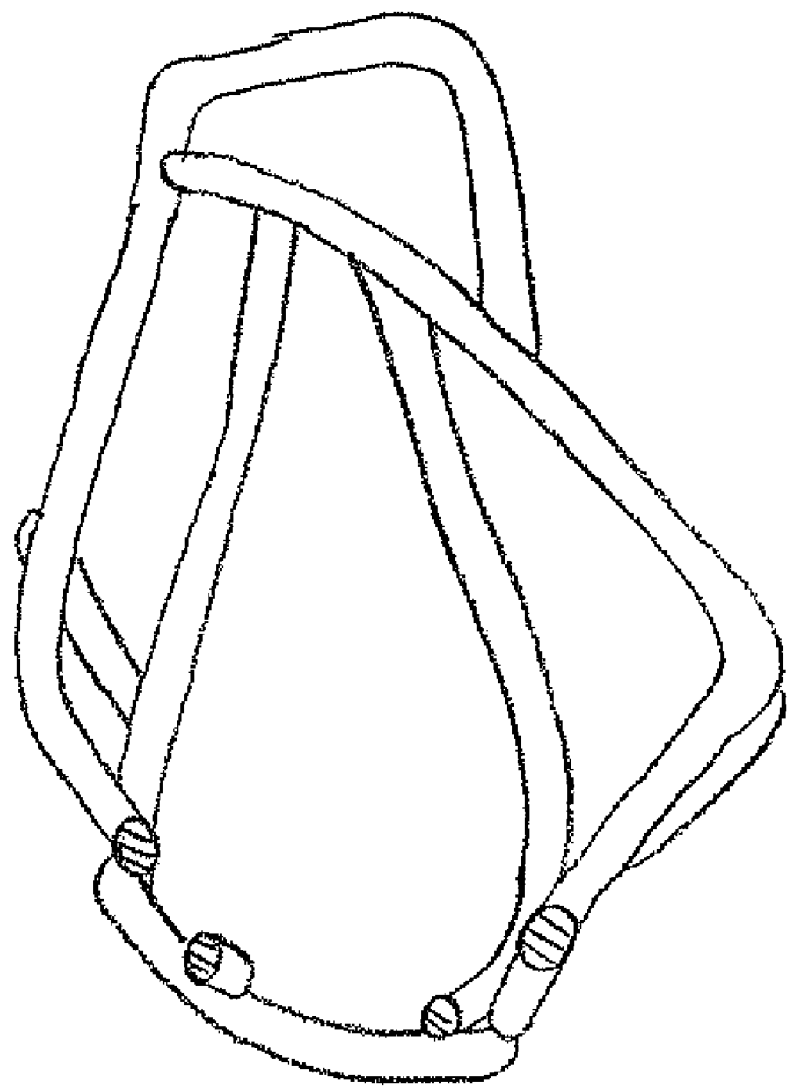

Providing further details of the construction of exemplary eyewear apparatus 100, FIG. 7 illustrates a cross-sectional view of the frame shown in FIG. 2 along line B-B. FIG. 8 illustrates a cross-sectional view of the frame shown in FIG. 2 along line C-C.

In a further embodiment of the present invention, compressible layers 106 provide gutters that divert perspiration away from the eyes, nose, and mouth of a user. The compressible layers 106 applied to the forehead base member 122 catch perspiration from the user's forehead and divert it to the side of the user's head. The compressible layers 106 applied to the cheek base member 120 catch perspiration from the nose and beneath the eyes of the user, and divert it to the side of the user's cheeks. The gutters can be provided throughout the length of compressible layers 106, or at isolated locations (e.g., at portions of the compressible layers 106 intended to contact a user's temple).

Figure 9A:
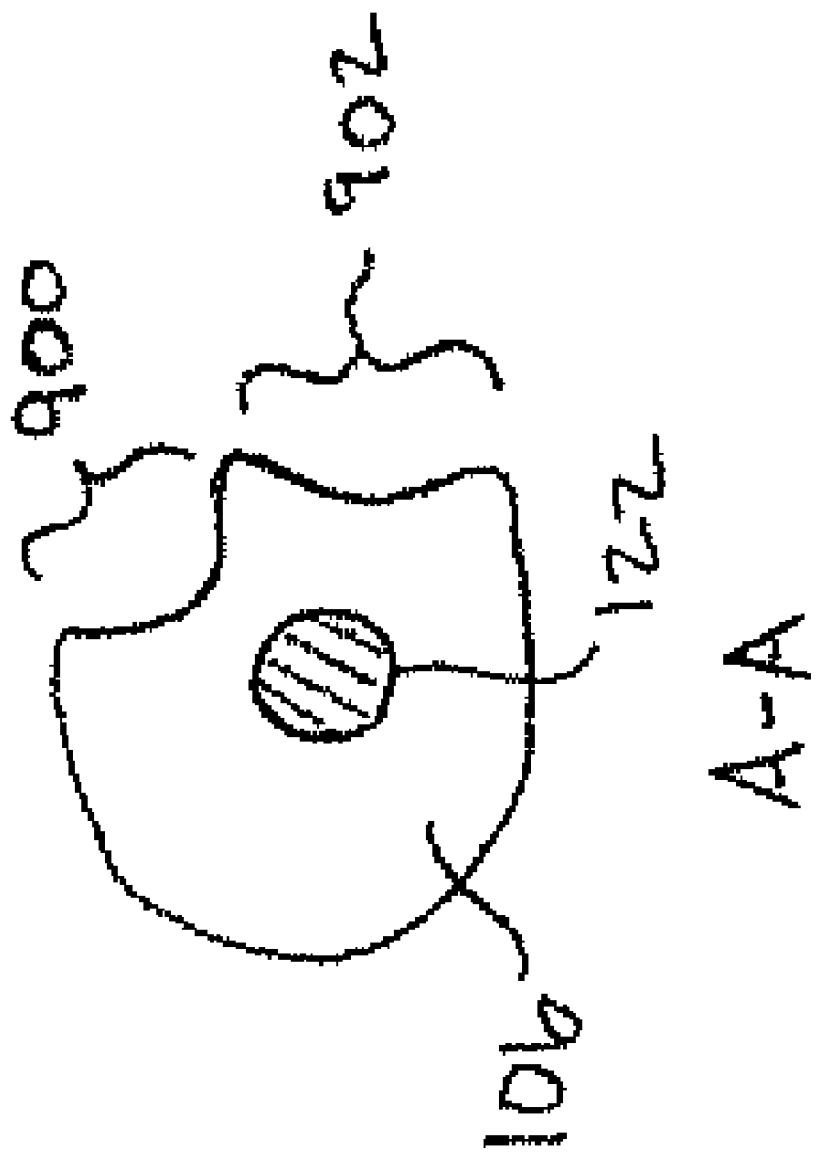
FIG. 9A is a schematic diagram of a cross-sectional view of a compressible layer having a perspiration gutter taken along line A-A in FIG. 1A, according to an embodiment of the present invention.

As an example, FIG. 9A illustrates a shape of a compressible layer 106 adapted to divert perspiration away from a user's eyes and mouth. As shown in this cross-sectional view, compressible layer 106 encases forehead base member 122 and includes a concave channel 900 that collects the perspiration and a contact portion 902 that contacts the user's face. The channel 900 can be raised toward the middle of eyewear apparatus 100 so that the perspiration flows down toward the ends of the eyewear apparatus 100. For example, the concave channel 900 of a gutter can slope down starting from an area proximate the main support 140 when the protective eyewear apparatus is worn by a user.

Compressible layers 106 can be constructed of any compressible material that is comfortable against a player's body, such as a foam or a thermoplastic elastomer. According to embodiments of the present invention, compressible layers 106 are applied to the frame of eyewear apparatus 100 by insert molding, reaction injection molding, spray application, rotational molding, dual extrusion, or casting. Compressible layers 106 are made of a material that is complementary to the material of the frame, such that the compressible layers 106 strongly bond to the frame, preferably without the use of adhesives or other intermediate bonding layers. Examples of suitable materials include nylon, urethane (TPU), sanoprene, polycarbonate, alcryln (partially crosslinked halogenated polyolefin alloy), styrene-butadiene-styrene, styrene-ethylene-butylene styrene, thermoplastic olefinic (TPO), thermoplastic vulcanizate (TPV), ethylene-propylene rubber (EPDM), flexible PVC, polyethylene, polypropylene, EVA, and ABS. Compressible layers 106 could also be formed from multiple laminated materials or fabric coverings.

Figure 9B:
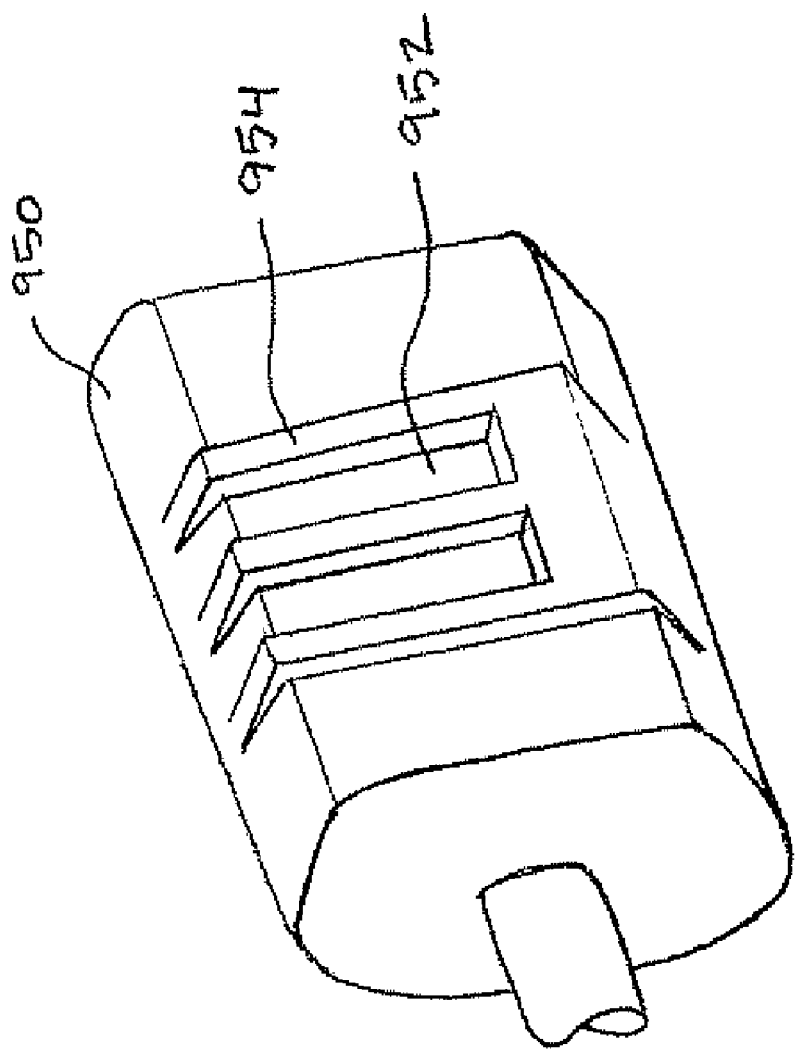
FIG. 9B is a schematic diagram of a portion of an exemplary textured compressible layer, according to an embodiment of the present invention.

If compressible layers 106 are not covered and directly contact a user's skin, compressible layers 106 can be made of anti-microbial silicone, to avoid skin irritations. The surface of compressible layers 106 can also be textured to help keep the eyewear apparatus 100 in place on the user's face when the user is sweating. FIG. 9B illustrates an example of a textured compressible layer 950. The depressions 952 of the textured surface hold the sweat, allowing the raised portions 954 of the textured surface to remain in direct contact with the skin to secure the eyewear apparatus 100 to the user's face. Although FIG. 9B shows a grooved textured surface, other textured surfaces can, of course, be used, such as dimples, nubs, ridges, or protuberances.

The textured surface can also be used in combination with gutters. For example, a textured surface can be applied to the faces of the gutters, or the textured surface can be applied to some portions of compressible layers 106 (e.g., in areas intended to contact the center of user's forehead) and the gutters can be applied to other portions (e.g., in areas intended to contact a user's temple).

In a further embodiment of the present invention, eyewear apparatus 100 includes a layer of performance fabric over compressible layers 106. This performance fabric can be disposed on the compressible layers 106 that cover the portions of eyewear apparatus 100 that contact the user, e.g., at cheek base members 120, which contact the user's cheeks, and at forehead base member 122, which contacts the user's lower forehead. In this case, the performance fabric, rather than the compressible layers 106, contacts the user's skin. The performance fabric is an air permeable material that moves moisture away from the user's skin and dries quickly. An example of a suitable performance fabric is Cool Max™ produced by INVISTA of Wichita, Kans.

Based on the features described above, the present invention provides critical eye protection, a large field of vision, and improved comfort. The eyewear apparatus 100 covers and protects the lower forehead, the eyes, the nose, and the upper cheeks of the user, and meets the ASTM F803 impact requirements. The configuration of the frame members, especially the use of a single vertical support bar (main support bar 140) in the field of vision, maximizes a user's unobstructed view, straight ahead, up and down, and side to side. The open air design of the protective cage 104 also avoids the glaring, fogging, rain beading, cracking, and scratching problems known to occur with traditional clear plastic lens goggles (e.g., polycarbonate goggles).

The compressible layers 106 provide a comfortable, compliant, and close fit with a user's face. In addition, when formed with gutters or textured surfaces, the compressible layers 106 keep perspiration away from the user's eyes, nose, and mouth to further increase comfort. When covered with a performance fabric, the compressible layers 106 also wick perspiration away from the user's skin.

Figure 10:
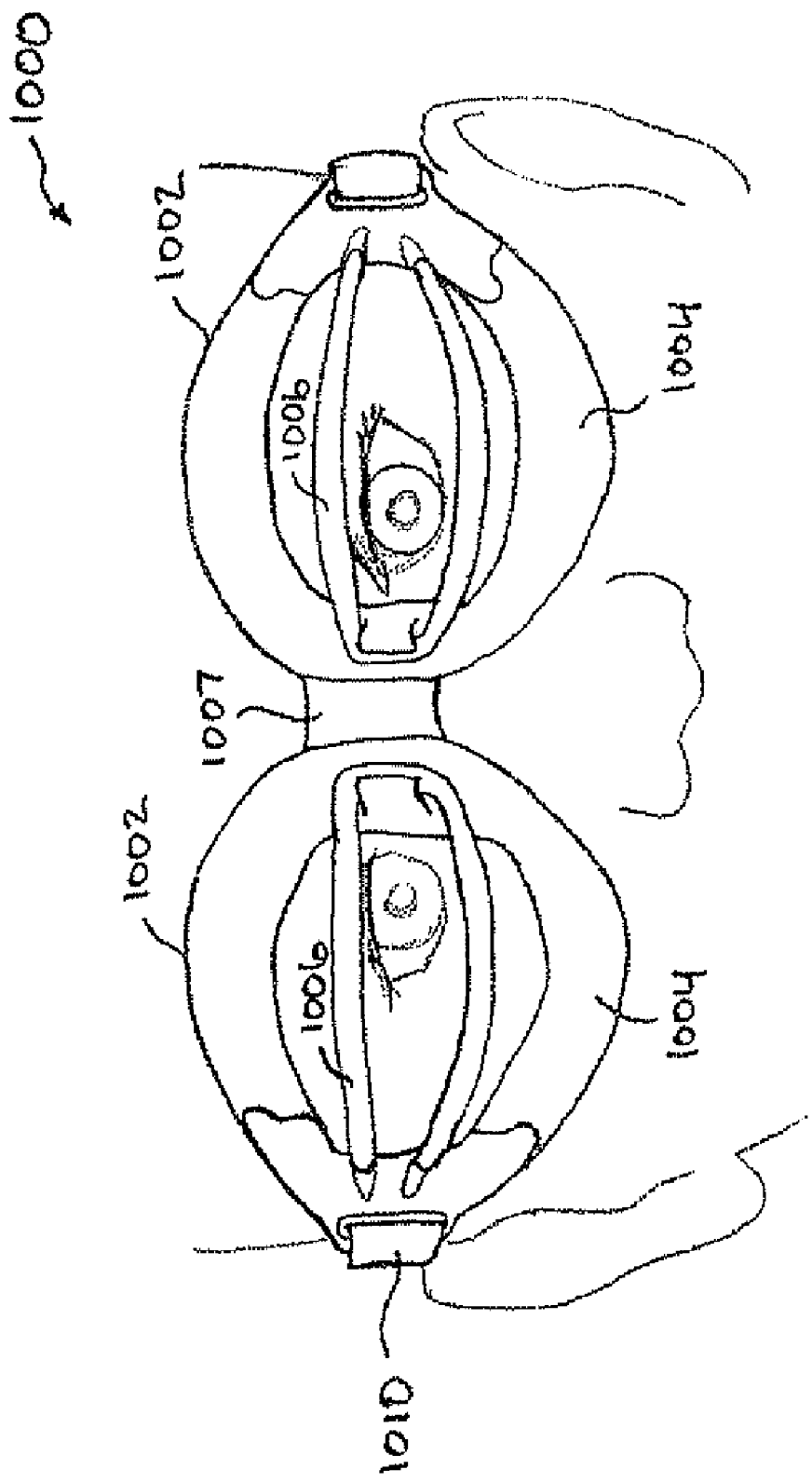
FIG. 10 is a schematic diagram of another exemplary protective eyewear apparatus, according to an alternative embodiment of the present invention.

FIG. 10 illustrates another protective eyewear apparatus 1000, according to an alternative embodiment of the present invention. In this alternative embodiment, eyewear apparatus 1000 provides separate eyepieces 1002 over each eye. Each eyepiece 1002 includes its own base 1004 and protective cage 1006. Base 1004 can be generally oval in shape and define an opening. Eyepieces 1002 are joined together by a bridge member 1007, which can be soft and flexible and made of an elastomer. An eyewear securing means 1010 attaches to each of the eyepieces 1002. Securing means 1010 could be any well known means for securing goggles, eyeglasses, or other eyewear apparatus to a user's face, for example, an elastic strap.

Protective cage 1006 can include an upper and lower bar as shown in FIG. 10, which both attach to base 1004 and span the opening of base 1004. The upper bar and the lower bar are spaced apart from each other and can be generally parallel and horizontal when the eyewear apparatus 1000 is worn by a user. The upper and lower bars can be attached by, for example, molding the base over the bars, mechanically fastening the wires to the base (e.g., using screws), or welding the bars to the base. In the embodiment of FIG. 10, protective cage 1006 is attached to base 1002 by both molding and mechanical means (described further below). The upper and lower bars can be formed from a single continuous member as shown in FIG. 10, or can be separate members.

Figure 11:
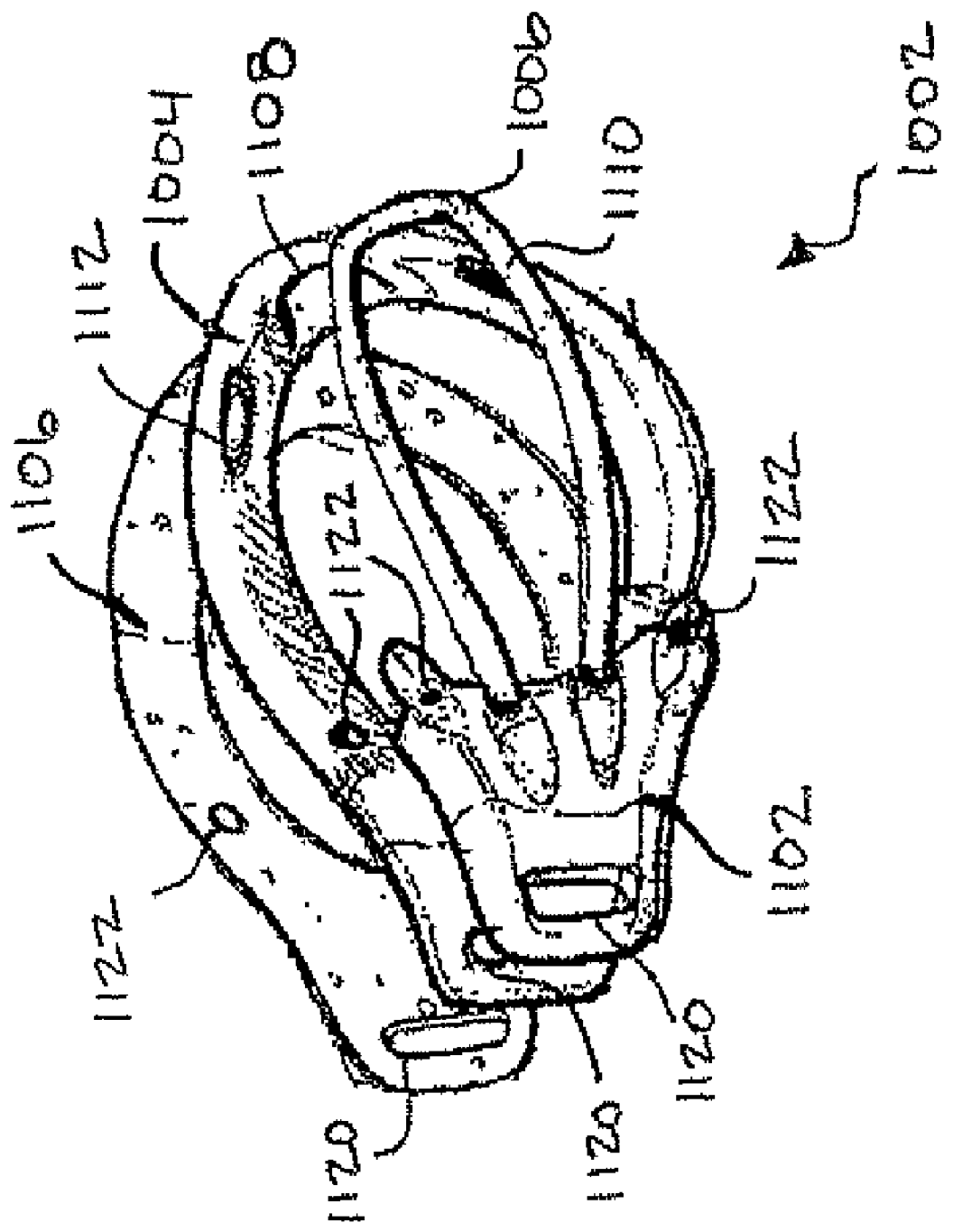
FIG. 11 is a schematic diagram of an exploded view of one eyepiece of the exemplary protective eyewear apparatus shown in FIG. 10.

FIG. 11 illustrates an exploded view of the right eyepiece 1002 of the protective eyewear apparatus 1000 of FIG. 10. As shown, eyepiece 1002 includes protective cage 1006, base 1004, and a pad 1106. Protective cage 1006 can include a wire 1110 and a wire retainer 1102. As shown, wire 1110 can be formed in a substantially "U" shape, with the ends of wire 1110 secured by wire retainer 1102. Wire retainer 1102 can be an injection molded or overmolded part that encloses the ends of wire 1110. Wire retainer 1102 is, for example, molded around the ends of wire 1110 and is made of an elastomer.

Wire 1110 provides the immediate protection over a user's eye and prevents objects from penetrating eyewear apparatus 1000 and contacting the user's eye. As such, wire 1110 must be of a strength sufficient to resist deformation upon impact by a standard lacrosse ball traveling at speeds typically encountered during play. In one embodiment, wire 1110 is 3.8 mm 1008 solid carbon steel wire, ASTM Standard, Section 03.05. Other suitable materials include other metals, metal alloys, composite materials, and synthetic materials.

Base 1004 provides the structure on which protective cage 1006 is mounted. Base 1004 can be more rigid than the wire retainer 1102 of the protective cage 1006. For example, if wire retainer 1102 is a flexible elastomer, then base 1004 could be a more rigid polycarbonate. As another example, base 1004 could be a wire encased in a foam or elastomer. Base 1004 transfers a point force (e.g., impact of a ball) imposed on the protective cage 1006 to a user's bones surrounding the eye and distributes the force over a wide surface area to minimize the chance of injury. In one configuration, base 1004 is a clear injection molded plastic, such as polycarbonate, and is generally oval in shape.

In one embodiment, as shown in FIG. 11, base 1004 includes a hook 1108 around which the closed end of wire 1110 is disposed. In this manner, hook 1108 further secures protective cage 1006 to base 1004. The hook can be disposed on a portion of the base disposed substantially between an eye and a nose of a user when the user wears the protective eyewear apparatus, with the wire retainer attached to the base on a side substantially opposite to the hook.

Base 1004 can also include at least one opening 1112 that receives a fastener that secures bridge member 1007 to base 1004. In one embodiment, this fastener is a mushroom shaped projection formed in bridge member 1007 that deforms through and snaps into the at least one opening 1112.

Pad 1106 is attached to base 1004 by, for example, an adhesive. In one embodiment, pad 1106 is made of laminated perforated shock absorbing foam or a compression molded foam. In another embodiment in which base 1004 is a wire, pad 1106 can be a compressible layer (e.g., foam or elastomer) encasing the wire.

Pad 1106 contacts the user's skin and provides form fitting comfort. In a further embodiment, the surface of pad 1106 that contacts the user's skin is covered with an air permeable performance fabric that moves moisture away from the user's skin and dries quickly. An example of a suitable performance fabric is Cool Max™ produced by INVISTA of Wichita, Kans.

In an embodiment of the present invention, as shown in FIG. 11, protective cage 1006, base 1004, and pad 1106 are further secured by one or more fasteners disposed in openings 1122 of each piece. Protective cage 1006, base 1004, and pad 1106 also include aligned openings 1120 that receive the securing means 1010 (FIG. 10).

Although the present invention has been discussed primarily in the context of women's lacrosse, one of ordinary skill in the art would appreciate that the protective eyewear apparatus of the present invention is equally applicable to both men and women, and to other sports and other non-sport activities. For example, the protective eyewear apparatus of the present invention could be used for field hockey, or for construction or manufacturing activities in which large objects may contact a person's face. Thus, notwithstanding the particular benefits of the present invention in the context of women's lacrosse, the present invention should be understood to be broadly applicable to any situation in which eye protection is needed.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims, and by their equivalents.

What is claimed is:

1. A protective eyewear apparatus comprising:
   a forehead member having
      a center portion,
      a first strap portion adjacent to the center portion, and
      a second strap portion adjacent to the center portion and on a side of the center portion opposite to the first strap portion;
   a cheek member having a first end connected to the forehead member approximately between the first strap portion and the center portion, and a second end connected to the forehead member approximately between the second strap portion and the center portion, the cheek member spaced apart from the forehead member to define a base;
   an upper bar extending between the forehead member and the cheek member, the upper bar having a first end connected to the cheek member and a second end connected to the cheek member;
   a lower bar extending between the forehead member and the cheek member, the lower bar having a first end connected to the cheek member and a second end connected to the cheek member, the upper bar disposed closer to the forehead member than the lower bar; and
   a main support bar connected to the cheek member, the upper bar, the lower bar, and the center portion of the forehead member, the main support bar being generally vertical when viewing the protective eyewear apparatus from a front view worn on a user's face.

2. The protective eyewear apparatus of claim 1, further comprising a compressible layer on the forehead member, the compressible layer defining a perspiration gutter.

3. The protective eyewear apparatus of claim 2, the perspiration gutter comprising a concave channel sloping down starting from an area proximate the main support bar when the protective eyewear apparatus is worn by a user.

4. The protective eyewear apparatus of claim 2, the compressible layer defining a perspiration gutter at an area of the compressible layer intended to contact a user's temple.

5. The protective eyewear apparatus of claim 2, the compressible layer having a textured surface, the textured surface comprising raised portions adapted to contact a user's skin and depressed portions adapted to hold perspiration.

6. The protective eyewear apparatus of claim 5, the textured surface comprising grooves.

7. The protective eyewear apparatus of claim 2, the compressible layer comprising one of foam and elastomer.

8. The protective eyewear apparatus of claim 1, further comprising a compressible layer on the cheek member, the compressible layer defining a perspiration gutter that slopes down in a direction away from the main support bar.

9. The protective eyewear apparatus of claim 1, the forehead member comprising a single continuous member.

10. The protective eyewear apparatus of claim 1, the first strap portion further connected to the cheek member to provide a first closed loop, and the second strap portion further connected to the cheek member to provide a second closed loop.

11. The protective eyewear apparatus of claim 10, further comprising a strap disposed though the first closed loop and the second closed loop.

12. The protective eyewear apparatus of claim 1, the main support bar, at the connection to the forehead member, being substantially perpendicular to the forehead member.

13. The protective eyewear apparatus of claim 1, further comprising:
   a first support bar connecting the forehead member and the upper bar;
   a second support bar connecting the forehead member and the upper bar, the first support bar and the second support bar disposed on opposite sides of the main support bar;
   a third support bar connecting the cheek member and the lower bar; and
   a fourth support bar connecting the cheek member and the lower bar, the third support bar and the fourth support bar disposed on opposite sides of the main support bar.

14. The protective eyewear apparatus of claim 1, the forehead member, the cheek member, the upper bar, the lower bar, and the main support bar comprising approximately 3.8 mm thick 1008 solid carbon steel wire.

15. The protective eyewear apparatus of claim 1, the upper bar, the lower bar, and the cheek member defining an opening that extends around a side of a head of a user wearing the protective eyewear apparatus to enable unobstructed peripheral vision.

16. The protective eyewear apparatus of claim 1, further comprising eyewear securing means attached to the first strap portion and the second strap portion of the forehead member.

17. The protective eyewear apparatus of claim 16, the eyewear securing means comprising an elastic swap.

18. The protective eyewear apparatus of claim 1, the forehead member, the cheek member, the upper bar, the lower bar, and the main support bar comprising composite resin.

19. The protective eyewear apparatus of claim 1, the center portion of the forehead member comprising a center concave portion, a left convex portion, and a right convex portion, when viewing the protective eyewear apparatus from a front view worn on the user's face,
   the cheek member comprising a center convex portion, a left concave portion, and a right concave portion, when viewing the protective eyewear apparatus from a front view worn on the user's face,
   the center concave portion of the forehead member vertically opposite to the center convex portion of the cheek member,
   the left convex portion of the forehead member vertically opposite to the left concave portion of the cheek member, and
   the right convex portion of the forehead member vertically opposite to the right concave portion of the cheek member.

20. The protective eyewear apparatus of claim 19, the forehead member and the cheek member separated by a vertical distance that decreases from a maximum measured between the left convex portion of the forehead member and the left concave portion of the cheek member to a minimum measured between the concave portion of the forehead member and the convex portion of the cheek member, to enable a wide field of vision.

21. A protective eyewear apparatus comprising:
a forehead member comprising a center concave portion, a left convex portion, and a right convex portion, when viewing the protective eyewear apparatus from a front view worn on a user's face;
a cheek member comprising
a first end connected to the forehead member on a side of the left convex portion of the forehead member opposite to the center concave portion of the forehead member, and
a second end connected to the forehead member on a side of the right convex portion of the forehead member opposite to the center concave portion of the forehead member,
the cheek member comprising a center convex portion, a left concave portion, and a right concave portion, when viewing the protective eyewear apparatus from a front view worn on the user's face,
the center concave portion of the forehead member vertically opposite to the center convex portion of the cheek member,
the left convex portion of the forehead member vertically opposite to the left concave portion of the cheek member,
the right convex portion of the forehead member vertically opposite to the right concave portion of the cheek member,
the forehead member and the cheek member separated by a vertical distance that decreases from a maximum measured between the left convex portion of the forehead member and the left concave portion of the cheek member to a minimum measured between the concave portion of the forehead member and the convex portion of the cheek member, to enable a wide field of vision;
an upper bar extending between the forehead member and the cheek member when viewing the protective eyewear apparatus from a front view worn on the user's face, the upper bar having a first end connected to the left concave portion of the cheek member and a second end connected to the right concave portion of the cheek member;
a lower bar extending between the forehead member and the cheek member when viewing the protective eyewear apparatus from a front view worn on the user's face, the lower bar having a first end connected to the left concave portion of the cheek member and a second end connected to the right concave portion of the cheek member, the lower bar being disposed closer to the cheek member than the upper bar; and
a main support bar connected to the upper bar and the lower bar, the main support bar being generally vertical when viewing the protective eyewear apparatus from a front view worn on the user's face.

22. The protective eyewear apparatus of claim 21, the main support bar having a first end connected to the concave portion of the forehead member and a second end connected to the convex portion of the cheek member.

23. The protective eyewear apparatus of claim 21, further comprising a compressible layer disposed on the forehead member, the compressible layer defining a gutter sloping down from the center of the forehead member when the protective eyewear apparatus is worn by the user.

24. The protective eyewear apparatus of claim 21, further comprising a compressible layer disposed on the forehead member, the compressible layer having a textured surface, the textured surface comprising raised portions adapted to contact the user's skin and depressed portions adapted to hold perspiration.

25. The protective eyewear apparatus of claim 24, the textured surface comprising grooves.

26. The protective eyewear apparatus of claim 21, the forehead member, the cheek member, the upper bar, the lower bar, and the main support bar comprising composite resin.

27. The protective eyewear apparatus of claim 21, the cheek member having a projecting portion that spans a user's nose such that the protective eyewear apparatus does not contact the user's nose when the protective eyewear apparatus is worn by the user.

28. The protective eyewear apparatus of claim 21, the forehead member further comprising
a first strap portion extending beyond a point at which the first end of the cheek member connects to the forehead member,
a second strap portion extending beyond a second point at which the second end of the cheek member connects to the forehead member.

29. The protective eyewear apparatus of claim 28, the first strap portion of the forehead member curved beyond the point at which the first end of the cheek member connects to the forehead member and attached to the cheek member to form a first closed loop,
the second strap portion of the forehead member curved beyond the point at which the second end of the cheek member connects to the forehead member and attached to the cheek member to form a second closed loop.

30. The protective eyewear apparatus of claim 29, further comprising a strap aft ached through the first closed loop and the second closed loop.

31. The protective eyewear apparatus of claim 21, further comprising a strap attached to the protective eyewear apparatus.

32. The protective eyewear apparatus of claim 21, further comprising:
a first support bar connecting the forehead member and the upper bar;
a second support bar connecting the forehead member and the upper bar, the first support bar and the second support bar disposed on opposite sides of the main support bar;
a third support bar connecting the cheek member and the lower bar;
a fourth support bar connecting the cheek member and the lower bar, the third support bar and the fourth support bar disposed on opposite sides of the main support bar.

* * * * *

UNITED STATES PATENT AND TRADEMARK OFFICE
CERTIFICATE OF CORRECTION

PATENT NO.         : 7,617,544 B2                                                     Page 1 of 1
APPLICATION NO.    : 11/832366
DATED              : November 17, 2009
INVENTOR(S)        : Helen M. Hahn and Dale W. Kohler It is certified that error appears in the above-identified patent and that said Letters Patent is hereby corrected as shown below:

At column 10, claim 11, line 2, replace "though" with --through--.

At column 10, claim 17, line 2, replace "swap" with --strap--.

At column 12, claim 30, line 2, replace "aft ached" with --attached--.

Signed and Sealed this

Twenty-first Day of September, 2010

David J. Kappos
*Director of the United States Patent and Trademark Office*